US011458139B2

(12) United States Patent
Rosen et al.

(10) Patent No.: US 11,458,139 B2
(45) Date of Patent: Oct. 4, 2022

(54) USE OF BRAF INHIBITORS FOR TREATING CUTANEOUS REACTIONS CAUSED BY TREATMENT WITH A MEK INHIBITOR

(71) Applicant: MEMORIAL SLOAN KETTERING CANCER CENTER, New York, NY (US)

(72) Inventors: Neal Rosen, New York, NY (US); Noa Shelach, Tel Aviv (IL)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 0 days.

(21) Appl. No.: 16/636,974

(22) PCT Filed: Aug. 8, 2018

(86) PCT No.: PCT/US2018/045834
§ 371 (c)(1),
(2) Date: Feb. 6, 2020

(87) PCT Pub. No.: WO2019/032717
PCT Pub. Date: Feb. 14, 2019

(65) Prior Publication Data
US 2020/0163967 A1 May 28, 2020

Related U.S. Application Data

(60) Provisional application No. 62/542,682, filed on Aug. 8, 2017.

(51) Int. Cl.
| *A61K 31/519* | (2006.01) |
| *A61K 31/4184* | (2006.01) |
| *A61K 31/428* | (2006.01) |
| *A61K 31/437* | (2006.01) |
| *A61K 31/4439* | (2006.01) |
| *A61K 31/4745* | (2006.01) |
| *A61K 31/506* | (2006.01) |
| *A61K 31/517* | (2006.01) |

(52) U.S. Cl.
CPC ........ *A61K 31/519* (2013.01); *A61K 31/4184* (2013.01); *A61K 31/428* (2013.01); *A61K 31/437* (2013.01); *A61K 31/4439* (2013.01); *A61K 31/4745* (2013.01); *A61K 31/506* (2013.01); *A61K 31/517* (2013.01)

(58) Field of Classification Search
CPC .............. A61K 31/519; A61K 31/4184; A61K 31/428; A61K 31/437; A61K 31/4439; A61K 31/4745; A61K 31/506; A61K 31/517; A61K 9/0019; A61K 9/0053; A61K 9/0014; A61K 31/416; A61K 31/44; A61P 17/00; A61P 35/00
See application file for complete search history.

(56) References Cited

U.S. PATENT DOCUMENTS

2019/0389862 A1* 12/2019 Shelach .................. A61P 17/10

FOREIGN PATENT DOCUMENTS

WO WO-2016/123679 A1 8/2016

OTHER PUBLICATIONS

Flaherty et al. (N Engl J Med. Nov. 2012 ; 367(18): 1694-1703, pp. 1-15 and supplemental pp. S1-S16).*
Sanlorenzo et al. (J Am Acad Dermatol 2014;71: p. 1102-1109).*
BC Cancer Agency, Symptom Management Guidelines: Acneiform Rash, p. 2 (Sep. 2016).
Boussemart et al., "Prospective study of cutaneous side-effects associated with the BRAF inhibitor vemurafenib: a study of 42 patients," Annals of Oncology, p. 1692 (Feb. 13, 2013).
Flaherty et al., "Combined BRAF and MEK inhibition in melanoma with BRAF V600 mutations," New England Journal of Medicine, p. 2 (Nov. 2012).
International Search Report and Written Opinion, PCT/US2018/045834, Memorial Sloan Kettering Cancer Center (dated Oct. 11, 2018).
Anforth, R., et al., "Acneiform eruptions: A common cutaneous toxicity of the MEK inhibitor trametinib: Acneiform eruptions and trametinib", Australasian Journal of Dermatology, 2013, vol. 55, No. 4, pp. 250-254, doi:10.1111/ajd.12124.
Escuin-Ordinas, H., et al., "Cutaneous wound healing through paradoxical MAPK activation by BRAF inhibitors", Nature Communications, 2016, vol. 7, p. 12348, doi:10.1038/ncomms12348.
Lacroix, J-P., et al., "Prospective study of cutaneous adverse effects associated with BRAF inhibitor dabrafenib and MEK inhibitor trametinib: A study of 12 patients ED—Lim Henry W", Journal of the American Academy of Dermatology, 2016, vol. 74, No. 5, doi:10.1016/J.JAAD.2016.02.271.
Manousaridis, I., et al., "Cutaneous side effects of inhibitors of the RAS/RAF/MEK/ERK signaling pathway and their management", Jeadv. Journal of the European Academy of Dermatology and Venereology, 2013, vol. 27, No. 1, pp. 1-8, doi: 10.1111/j.1468 3083.2012.04546.x.

* cited by examiner

*Primary Examiner* — Robert H Havlin
(74) *Attorney, Agent, or Firm* — Foley & Lardner LLP (57) ABSTRACT

The present technology relates to compositions comprising BRAF inhibitors and uses thereof for treating and/or preventing a MEK inhibitor-associated cutaneous condition in a subject. Kits for use in practicing the methods are also provided.

11 Claims, 2 Drawing Sheets

USE OF BRAF INHIBITORS FOR TREATING CUTANEOUS REACTIONS CAUSED BY TREATMENT WITH A MEK INHIBITOR

CROSS-REFERENCE TO RELATED APPLICATIONS

This application is a National Stage Application of PCT/US2018/045834, filed Aug. 8, 2018, which claims the benefit of and priority to U.S. Provisional Patent Application No. 62/542,682, filed Aug. 8, 2017, the entire contents of which are incorporated herein by reference.

TECHNICAL FIELD

The present technology relates to compositions comprising BRAF inhibitors and uses thereof for treating and/or preventing a MEK inhibitor-associated cutaneous condition in a subject.

BACKGROUND

The following description of the background of the present technology is provided simply as an aid in understanding the present technology and is not admitted to describe or constitute prior art to the present technology.

MEK (Mitogen-activated protein kinase, also known as MAP2K, MEK, and MAPKK) is a kinase enzyme which phosphorylates mitogen-activated protein kinase (MAPK). A mitogen-activated protein kinase (MAPK or MAP kinase) is a serine/threonine-specific protein kinase which is involved in various cell signaling pathways and regulates cell functions including proliferation, gene expression, differentiation, mitosis, cell survival and apoptosis. The activators of p38 (MKK3 and MKK6), JNK (MKK4 and MKK7), and ERK (MEK1 and MEK2) define independent MAP kinase signal transduction pathways.

Various therapeutic agents which target these pathways are used in the treatment of various related diseases, such as, melanoma, lung cancer, colorectal cancer, brain cancer, multiple myeloma, pancreatic cancer, and neurofibromatosis. The therapeutic agents (inhibitors) include kinase inhibitors, such as Trametinib and Cobimetinib.

The ability of MEK inhibitors to block specific molecular pathways driving uncontrolled cellular division in cancer has resulted in a decreased incidence of serious systemic adverse events associated with chemotherapy. However, cutaneous adverse events caused by MEK inhibitors have been reported, including acneiform (papulopustular) rash, abnormal scalp, facial hair and/or eyelash growth, paronychia with or without pyogenic granulomas and telangiectasia.

SUMMARY

In one aspect, the present disclosure provides a method for treating or preventing a MEK inhibitor-associated cutaneous condition in a subject in need thereof comprising administering to the subject an effective amount of at least one BRAF inhibitor to said subject, thereby treating the MEK inhibitor-associated cutaneous condition. Additionally or alternatively, in some embodiments of the methods of the present technology, administration of the at least one BRAF inhibitor results in an increase in MAPK activation in the subject compared to that observed in the subject prior to administration.

Additionally or alternatively, in some embodiments of the methods of the present technology, the MEK inhibitor-associated cutaneous condition is selected from the group consisting of acneiform rash, papulopustular rash, abnormal scalp hair growth, abnormal facial hair growth, abnormal hair growth, abnormal eyelash growth, paronychia with or without pyogenic granulomas, and telangiectasia. Additionally or alternatively, in some embodiments of the methods of the present technology, the MEK inhibitor-associated cutaneous condition is acneiform rash.

Additionally or alternatively, in some embodiments of the methods of the present technology, the subject is treated with a MEK inhibitor, prior to administration of the at least one BRAF inhibitor. Additionally or alternatively, in some embodiments of the methods of the present technology, the MEK inhibitor is selected from the group consisting of Trametinib (GSK1120212), Cobimetinib (XL518), Binimetinib (MEK162), Selumetinib, PD-325901, CI-1040, PD035901, UO126, TAK-733, and any combination thereof.

Additionally or alternatively, in some embodiments of the methods of the present technology, the at least one BRAF inhibitor is selected from the group consisting of BAY43-9006 (Sorafenib), LGX818 (encorafenib), PLX4032 (vemurafenib), GSK2118436 (dabrafenib), ARQ197 (Tivatinib), GSK1120212 (trametinib), ARQ736, ARQ680, AZ628, CEP-32496, GDC-0879, NMS-P186, NMS-P349, NMS-P383, NMS-P396, NMS-P730, PLX3603 (R05212054), PLX4720 (difluorophenyl-sulfonamine), PF-04880594, PLX4734, RAF265, R04987655, SB590885, BMS908662, WYE-130600, TAK632, MLN 2480, XL281, LUT001, LUT156, LUT192, LUT195, LUT197, and any combination thereof.

Additionally or alternatively, in some embodiments of the methods of the present technology, the at least one BRAF inhibitor is administered orally, topically, intranasally, systemically, intravenously, subcutaneously, intraperitoneally, intradermally, intraocularly, iontophoretically, transmucosally, or intramuscularly. Additionally or alternatively, in some embodiments of the methods of the present technology, the topical administration comprises local administration to the skin of the subject.

In another aspect, the present disclosure provides a kit comprising at least one BRAF inhibitor and instructions for treating or preventing a MEK inhibitor-associated cutaneous condition in a subject in need thereof. Additionally or alternatively, in some embodiments, the MEK inhibitor-associated cutaneous condition is selected from the group consisting of acneiform rash, papulopustular rash, abnormal scalp hair growth, abnormal facial hair growth, abnormal hair growth, abnormal eyelash growth, paronychia with or without pyogenic granulomas and telangiectasia.

Additionally or alternatively, in some embodiments, the at least one BRAF inhibitor is formulated for oral, topical, intranasal, systemic, intravenous, subcutaneous, intraperitoneal, intradermal, intraocular, iontophoretical, transmucosal, or intramuscular administration.

Additionally or alternatively, in some embodiments, the at least one BRAF inhibitor is formulated in a dosage form selected from the group consisting of a tablet, a capsule, a liquid, a suspension, a powder, an ointment, a cream, a gel, a hydrogel, a balm, a foam, a spray, a lotion, a liquid and a dermal patch. Additionally or alternatively, in some embodiments, administration of the at least one BRAF inhibitor results in an increase in MAPK activation in a subject compared to that observed in the subject prior to administration.

In another aspect, the present disclosure provides a method for treating or preventing acneiform rash in a subject in need thereof, comprising administering an effective amount of at least one BRAF inhibitor to the subject. The acneiform rash may be a side effect caused by treatment of the subject with a MEK inhibitor.

Additionally or alternatively, in some embodiments of the methods of the present technology, the at least one BRAF inhibitor is selected from the group consisting of BAY43-9006 (Sorafenib), LGX818 (encorafenib), PLX4032 (vemurafenib), GSK2118436 (dabrafenib), ARQ197 (Tivatinib), GSK1120212 (trametinib), ARQ736, ARQ680, AZ628, CEP-32496, GDC-0879, NMS-P186, NMS-P349, NMS-P383, NMS-P396, NMS-P730, PLX3603 (R05212054), PLX4720 (difluorophenyl-sulfonamine), PF-04880594, PLX4734, RAF265, R04987655, SB590885, BMS908662, WYE-130600, TAK632, MLN 2480, XL281, LUT001, LUT156, LUT192, LUT195, LUT197, and any combination thereof.

Additionally or alternatively, in some embodiments of the methods of the present technology, the at least one BRAF inhibitor is administered orally, topically, intranasally, systemically, intravenously, subcutaneously, intraperitoneally, intradermally, intraocularly, iontophoretically, transmucosally, or intramuscularly.

DETAILED DESCRIPTION

BRAF is a signal transduction protein kinase involved in the regulation of the mitogen-activated protein kinase (MAPK or ERK) signaling pathway. Mutations in BRAF can induce constitutive signaling through the MAPK pathway which may result in uncontrolled cell proliferation. Use of BRAF inhibitors have been demonstrated to be associated with inhibition of MAPK signaling, as determined by the inhibition or reduction in the level of phosphorylated ERK, which is the downstream effector of BRAF.

Figure 1A:
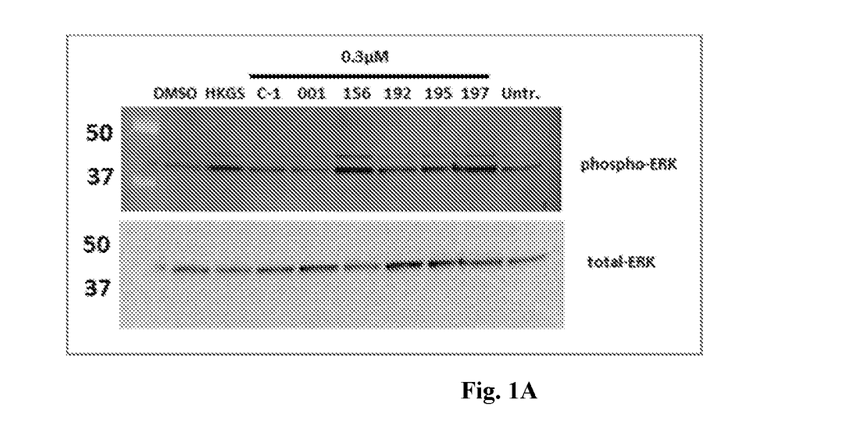
FIG. 1A shows the activation of ERK in HEKa following treatment with C1, LUT001, LUT156, LUT192, LUT195, and LUT197 at a concentration of 0.3 μM.
Figure 1B:
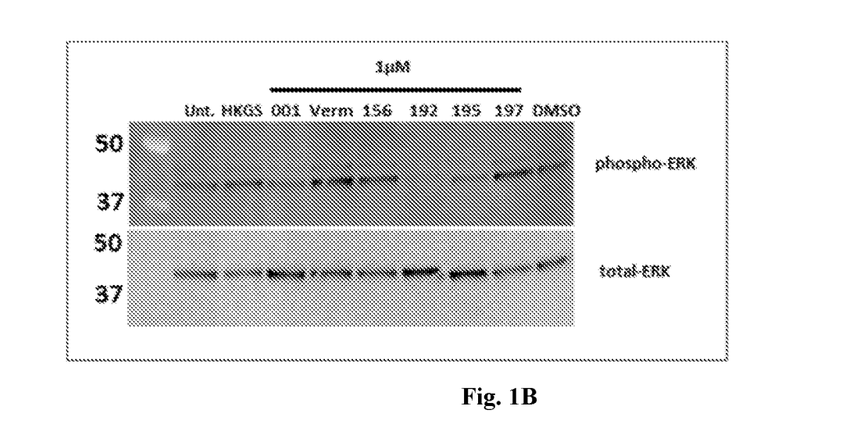
FIG. 1B shows the activation of ERK in HEKa following treatment with LUT001, vemurafenib, LUT156, LUT192, LUT195, and LUT197 at a concentration of 1 μM.
Figure 1C:
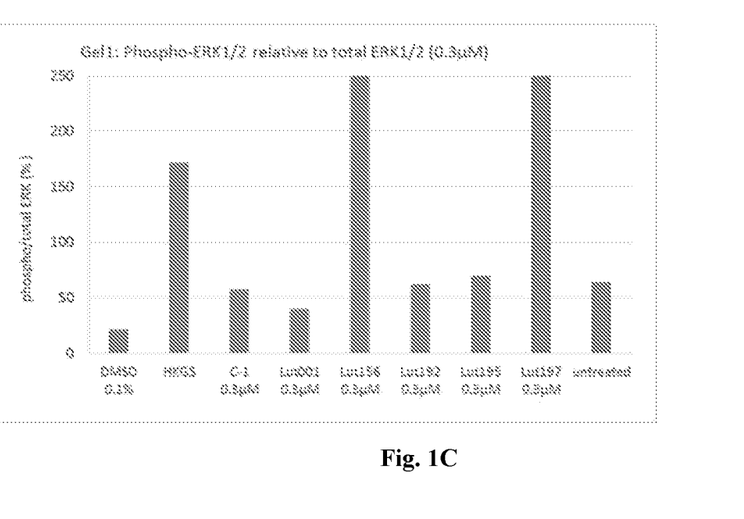
FIG. 1C shows the Phospho-ERK1/2 vs total ERK1/2 following treatment with C1, LUT001, LUT156, LUT192, LUT195 and LUT197 at a concentration of 0.3 μM.
Figure 1D:
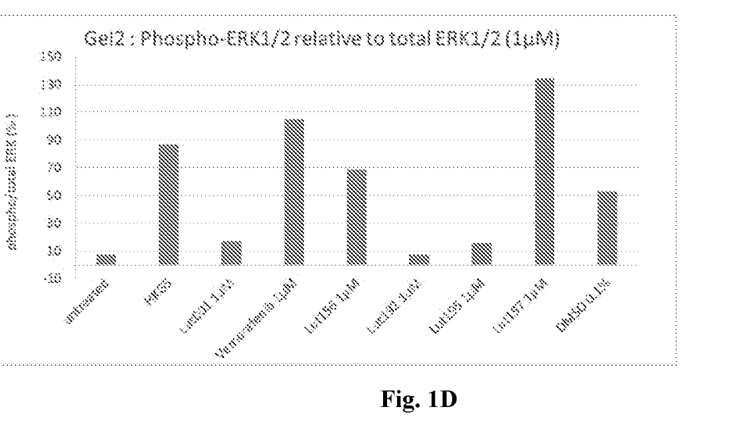
FIG. 1D shows the Phospho-ERK1/2 vs total ERK1/2 following treatment with LUT001, vemurafenib, LUT156, LUT192, LUT195 and LUT197 at a concentration of 1 μM.

The present disclosure demonstrates that BRAF inhibitors can unexpectedly induce the opposite effect of activating MAPK signaling in BRAF wild-type cells (as determined by increased levels of phosphorylated ERK). For example, FIGS. 1A-D demonstrate the significant activation of ERK (as determined by an increase in the relative amount of Phosphorylated ERK) in human primary keratinocytes (HEKa) following treatment with LUT156, LUT197 (FIGS. 1A and 1C) or vemurafenib (FIGS. 1B and 1D) BRAF inhibitors, while LUT001, LUT192, and LUT195 generated a moderate effect in HEKa. These results demonstrate the unexpected paradoxical effect of various BRAF inhibitors with respect to activating downstream MAPK (ERK) in keratinocytes cells. Further, the results demonstrate the different efficacies of various BRAF inhibitors at varying dosages (concentration) with respect to activating ERK.

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including orally, intranasally, parenterally (intravenously, intramuscularly, intraperitoneally, or subcutaneously), intratumorally, or topically. Administration includes self-administration and the administration by another.

As used herein, the terms "BRAF", "B-Raf", "Braf" and "BRaf" may be used interchangeably. The terms relate to serine/threonine-protein kinase BRAF, which is involved is cellular signaling pathways. The term inhibitor with respect to BRAF is directed to any one or more agents (drugs), compounds or molecules that can affect activity and/or expression of a wild type (WT) or mutant BRAF protein. The inhibitor may be selective or non-selective. In some embodiments, the inhibitor may exhibit a paradoxical effect, in which the inhibitor induces increased MAPK activity, for example, in cells where the target BRAF is a WT BRAF. BRAF inhibitors are known in the art. In some embodiments, the BRAF inhibitor may include a compound, a derivative thereof, an acceptable salt thereof and/or a solvate thereof.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or condition, a positive control (a compound or composition known to exhibit the desired therapeutic effect) and a negative control (a subject or a sample that does not receive the therapy or receives a placebo) are typically employed.

As used herein, the terms "cutaneous reaction", "cutaneous adverse reaction" "cutaneous adverse event" and "cutaneous condition" may be used interchangeably and are directed to a skin (cutaneous) condition that has developed, arose, initiated, been induced, been caused, or evolved as a result of treatment with a MEK inhibitor. In some embodiments, the skin condition is a side effect of the treatment with the MEK inhibitor.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

As used herein, the terms "MEK", "ERK", "MAPKK" may be used interchangeably. The terms relate to serine/threonine-protein kinase MEK, which is involved in cellular signaling pathways. The term inhibitor with respect to MEK is directed to any one or more agents (drugs), compounds or molecules that can affect activity and/or expression of a WT or mutant MEK protein. The inhibitor may be selective or non-selective.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the terms "individual", "patient", or "subject" are used interchangeably and refer to an individual organism, a vertebrate, a mammal, or a human. In certain embodiments, the individual, patient or subject is a human.

As used herein, "pharmaceutical composition" refers to therapeutically effective amounts of the active agents of the present technology, together with suitable (acceptable) diluents, preservatives, solubilizers, emulsifiers, adjuvants carriers or other pharmaceutically acceptable excipients.

As used herein, "pharmaceutically acceptable carrier" refers to a diluent or vehicle which is used to enhance the delivery and/or pharmacokinetic properties of a pharmaceutical active agent with which it is formulated, but has no therapeutic effect of its own, nor does it induce or cause any significant undesirable or untoward effect or adverse reaction in the subject. Pharmaceutically acceptable carriers are well known to those skilled in the art and include, but are not limited to phosphate buffer and/or saline. Additionally, such pharmaceutically acceptable carriers may be aqueous or non-aqueous solutions, suspensions, gels or emulsions.

As used herein, "prevention" or "preventing" of a disorder or condition refers to one or more compounds that, in a statistical sample, reduces the occurrence of the disorder or condition in the treated sample relative to an untreated control sample, or delays the onset of one or more symptoms of the disorder or condition relative to the untreated control sample.

As used herein, a "sample" or "biological sample" refers to a body fluid or a tissue sample isolated from a subject. In some cases, a biological sample may consist of or comprise whole blood, platelets, red blood cells, white blood cells, plasma, sera, urine, feces, epidermal sample, vaginal sample, skin sample, cheek swab, sperm, amniotic fluid, cultured cells, bone marrow sample, tumor biopsies, aspirate and/or chorionic villi, cultured cells, endothelial cells, synovial fluid, lymphatic fluid, ascites fluid, interstitial or extracellular fluid and the like. The term "sample" may also encompass the fluid in spaces between cells, including gingival crevicular fluid, bone marrow, cerebrospinal fluid (CSF), saliva, mucus, sputum, semen, sweat, urine, or any other bodily fluids. Samples can be obtained from a subject by any means including, but not limited to, venipuncture, excretion, ejaculation, massage, biopsy, needle aspirate, lavage, scraping, surgical incision, or intervention or other means known in the art. A blood sample can be whole blood or any fraction thereof, including blood cells (red blood cells, white blood cells or leukocytes, and platelets), serum and plasma.

"Treating", "treat", or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment or prevention of medical diseases and conditions as described are intended to mean "substantial," which includes total but also less than total treatment or prevention, and wherein some biologically or medically relevant result is achieved. The treatment may be a continuous prolonged treatment for a chronic disease or a single, or few time administrations for the treatment of an acute condition.

Compositions Including BRAF Inhibitors

In any embodiment herein, the at least one BRAF inhibitor may comprise or consist of any suitable active agent or drug that can inhibit activity or expression of BRAF. Additionally or alternatively, in some embodiments, the BRAF-inhibitor may be selected from the group consisting of BAY43-9006 (Sorafenib), LGX818 (encorafenib), PLX4032 (vemurafenib), GSK2118436 (dabrafenib), ARQ197 (Tivatinib), GSK1120212 (trametinib), ARQ736, ARQ680, AZ628, CEP-32496, GDC-0879, NMS-P186, NMS-P349, NMS-P383, NMS-P396, NMS-P730, PLX3603 (R05212054), PLX4720 (difluorophenyl-sulfonamine), PF-04880594, PLX4734, RAF265, R04987655, SB590885, BMS908662, WYE-130600, TAK632, MLN 2480, XL281, LUT001, LUT156, LUT192, LUT195, LUT197, and combinations thereof. Each possibility is a separate embodiment.

In any embodiment herein, the administration of the at least one BRAF inhibitor results in an increase in MAPK activation in the subject compared to that observed in the subject prior to administration.

In any embodiment herein, the MEK inhibitor may comprise or consist of any suitable active agent or drug that can inhibit activity and/or expression of MEK. In some embodiments, the MEK inhibitor is a MEK1 inhibitor. Additionally or alternatively, in some embodiments, the MEK inhibitor is a MEK2 inhibitor. Additionally or alternatively, in some embodiments, the MEK inhibitor may be selected from: Trametinib (GSK1120212), Cobimetinib (XL518), Binimetinib (MEK162), Selumetinib, PD-325901, CI-1040, PD035901, UO126, TAK-733, or any combination thereof.

Without wishing to be bound by theory, it is believed that BRAF inhibitors that unexpectedly promote MAPK activation are suitable drug candidates for the treatment or prevention of a cutaneous reaction caused by treatment with a MEK inhibitor. By way of example only, it is believed that keratinocytes are the likely site of MEK inhibitor-associated cutaneous side-effects, and the inhibition of MEK and/or its downstream effectors in keratinocytes may be the mechanism underlying this side effect. The present disclosure provides BRAF inhibitor compounds LUT001, LUT156, LUT192, LUT195, and LUT197 (see structures below):

In any embodiment herein, the BRAF inhibitors of the present technology exhibit an unexpected MAPK effect and are suitable for the treatment or prevention of a cutaneous reaction caused by treatment with a MEK inhibitor. Additionally or alternatively, in some embodiments, the MEK inhibitor treatment is anti-cancer treatment administered to a subject suffering from cancer.

In any embodiment herein, the composition for use in the present disclosure comprises a therapeutically effective amount of at least one BRAF inhibitor, and a pharmaceutically acceptable carrier. Additionally or alternatively, in some embodiments, the pharmaceutical composition includes at least one BRAF inhibitor and a pharmaceutically acceptable carrier.

In any embodiment herein, the pharmaceutical composition may be formulated in any of a number of forms including formulations for systemic, enteral, parenteral or topical administration. In any embodiment herein, the composition for use in the present technology comprises a therapeutically effective amount of at least one BRAF inhibitor, and a pharmaceutically acceptable carrier, and may optionally be systemically or topically administered.

In any embodiment herein, the at least one BRAF inhibitor may be suitably formulated as inclusion complexes, nano-emulsions and microemulsions. In any embodiment herein, the pharmaceutical composition may be formulated in any of a number of forms suitable for dermatological, topical and/or local administration, such as for example, a gel, a suspension, an ointment, a lotion, a liquid, a solution, an emulsion or microemulsion, a film, a cement, a powder, a glue, an aerosol, a spray, a foam, a patch, a bandage, and the like and combinations thereof. Each possibility is a separate embodiment.

In any embodiment herein, the dosage administered and/or the dosage regime is dependent upon the age, health, weight, severity of the cutaneous condition of the subject, the use of treatment with MEK inhibitors, frequency of treatment, and the nature of the desired effect. Each possibility is a separate embodiment.

In any embodiment herein, the amount and nature of the BRAF inhibitor in any unit dosage form comprises a therapeutically effective amount which may vary depending on the recipient subject, frequency of administration, the MEK inhibitor(s) treatment, site and severity of the cutaneous condition, and the like. Each possibility is a separate embodiment. In any embodiment herein, the concentration, amount or percentage of the at least one BRAF inhibitor in the composition may vary widely, and may depend on the volume, viscosity, dosage form, etc. of the formulation, as well as the administration regime.

In any embodiment herein, the pharmaceutical composition may further include at least one additional active agent capable of treating or ameliorating the cutaneous condition.

In any embodiment herein, the pharmaceutical compositions of the present technology may be manufactured in a manner which is itself known to one skilled in the art, for example, by means of conventional mixing, granulating, dragee-making, softgel encapsulation, dissolving, extracting, or lyophilizing processes.

In any embodiment herein, the at least one BRAF inhibitor may be administered with one or more active agents, in a single composition or in separate compositions. Each possibility is a separate embodiment.

In any embodiment herein, the at least one BRAF inhibitor (or a pharmaceutical composition comprising the same) may be administered prior to, concomitantly with, or after administration of an additional active agent (or a pharmaceutical composition comprising the same). Each possibility is a separate embodiment. In any embodiment herein, the pharmaceutical composition may be delivered in a controlled release system.

In any embodiment herein, the at least one BRAF inhibitor can be administered to using any available conventional methods and routes suitable for delivery of conventional drugs, including systemic or localized routes. In general, routes of administration contemplated by the present technology include, but are not necessarily limited to, enteral, parenteral, or inhalational routes.

In any embodiment herein, parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery. Where systemic delivery is desired, administration can typically involve invasive or systemically absorbed topical or mucosal administration of pharmaceutical preparations.

In any embodiment herein, the at least one BRAF inhibitor can also be delivered to the subject by enteral administration. Enteral routes of administration include, but are not necessarily limited to, oral and rectal (e.g., using a suppository) delivery.

Additionally or alternatively, in some embodiments, the composition is formulated for topical administration to body surfaces. Non-limiting examples of formulations for topical use include cream, ointment, lotion, gel, foam, suspension, aqueous or cosolvent solutions, salve and sprayable liquid form. Other suitable topical product forms for the compositions of the present technology include, for example, emulsion, mousse, foam, lotion, solution and serum. Additional suitable topical product forms include patches, bandages, and the like.

In any embodiment herein, the pharmaceutical composition can be in solid or liquid form such as tablets, powders, capsules, pellets, solutions, suspensions, elixirs, emulsions, gels, creams, ointments, balms or suppositories. Pharmaceutically acceptable carriers include gums, starches, sugars, cellulosic materials, and mixtures thereof. The composition can also be administered by intravenous, intra-arterial, or intramuscular injection of a liquid preparation, oral administration of a liquid or solid preparation, or by topical application. Administration can also be accomplished by use of a rectal suppository.

In any embodiment herein, the preparation of pharmaceutical compositions which contain an active agent is well known in the art. Typically, such compositions are prepared as aerosols of the active agent delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients that are pharmaceutically acceptable and compatible with the active agent. Suitable excipients are, for example, water, saline, dextrose, glycerol, ethanol, or the like and combinations thereof.

In any embodiment herein, if desired, the composition can contain in addition minor amounts of excipients such as wetting or emulsifying agents and/or pH buffering agents, which enhance the effectiveness of the active ingredient.

In any embodiment herein, the at least one BRAF inhibitor and/or additional active agent can be formulated into the composition as neutralized pharmaceutically acceptable salt forms, whenever feasible. Pharmaceutically acceptable salts include the acid addition salts, which are formed with inorganic acids such as, for example, hydrochloric or phosphoric acids, or such organic acids as acetic, methanesulfonic, benzene sulfonic, naphthalene sulfonic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Additionally or alternatively, in some embodiments, the pharmaceutical compositions can be delivered in a vesicle, such as, for example, a liposome. In any embodiment herein, for topical administration to body surfaces such as skin for example, compositions like creams, ointments, gels, lotions, solutions, co-solvent solutions, suspensions, patches, bandages, liquids, foams and the like may be used. The at least one BRAF inhibitor or their pharmaceutically acceptable derivatives such as salts, hydrates, and the like are conveniently prepared and applied as solutions, suspensions, or emulsions in a pharmaceutically acceptable diluent with or without a pharmaceutical carrier.

Also disclosed herein are kits with unit doses of suitable BRAF inhibitors, such as, oral doses, injectable doses, or topical doses. In any embodiment herein, in addition to the containers containing the unit doses, the kits may comprise an informational package insert describing the use and expected benefits of the at least one BRAF inhibitor in treating or preventing a MEK inhibitor-associated cutaneous condition.

Therapeutic Methods

The following discussion is presented by way of example only, and is not intended to be limiting.

One aspect of the present technology includes methods of treating a disease or condition characterized by elevated expression levels and/or increased activity of BRAF. Additionally or alternatively, in some embodiments, the present technology includes methods of treating a MEK inhibitor-associated cutaneous condition such as acneiform rash (papulopustular rash), paronychia with or without pyogenic granulomas, and/or telangiectasia.

In one aspect, the present disclosure provides a method for treating a MEK inhibitor-associated cutaneous condition in a subject in need thereof, comprising administering to the subject an effective amount of at least one BRAF inhibitor selected from the group consisting of BAY43-9006 (Sorafenib), LGX818 (encorafenib), PLX4032 (vemurafenib), GSK2118436 (dabrafenib), ARQ197 (Tivatinib), GSK1120212 (trametinib), ARQ736, ARQ680, AZ628, CEP-32496, GDC-0879, NMS-P186, NMS-P349, NMS-P383, NMS-P396, NMS-P730, PLX3603 (R05212054), PLX4720 (difluorophenyl-sulfonamine), PF-04880594, PLX4734, RAF265, R04987655, SB590885, BMS908662, WYE-130600, TAK632, MLN 2480, XL281, LUT001, LUT156, LUT192, LUT195, LUT197, and any combination thereof.

In some embodiments, the subject has been treated with a MEK inhibitor prior to administration of the at least one BRAF inhibitor. Additionally or alternatively, in some embodiments, the MEK inhibitor is selected from the group consisting of Trametinib (GSK1120212), Cobimetinib (XL518), Binimetinib (MEK162), Selumetinib, PD-325901, CI-1040, PD035901, UO126, TAK-733, and any combination thereof.

In some embodiments, the subject is diagnosed as having, suspected as having, or at risk of having a disease or condition characterized by elevated expression levels and/or increased activity of BRAF. Additionally or alternatively, in some embodiments, the subject is diagnosed as having a MEK inhibitor-associated cutaneous condition such as acneiform rash (papulopustular rash), paronychia with or without pyogenic granulomas, and/or telangiectasia. In some embodiments, the subject may exhibit one or more mutations in BRAF, KRAS and MEK, and are detectable using techniques known in the art.

In therapeutic applications, compositions or medicaments comprising at least one BRAF inhibitor disclosed herein are administered to a subject suspected of, or already suffering from such a disease or condition (such as, a subject diagnosed with a disease or condition characterized by elevated expression levels and/or increased activity of BRAF and/or a subject diagnosed with a MEK inhibitor-associated cutaneous condition such as acneiform rash (papulopustular rash), paronychia with or without pyogenic granulomas, and/or telangiectasia), in an amount sufficient to cure, or at least partially arrest, the symptoms of the disease, including its complications and intermediate pathological phenotypes in development of the disease.

Subjects suffering from a disease or condition characterized by elevated expression levels and/or increased activity of BRAF and/or a subject diagnosed with a MEK inhibitor-associated cutaneous condition such as acneiform rash (papulopustular rash), paronychia with or without pyogenic granulomas, and/or telangiectasia can be identified by any or a combination of diagnostic or prognostic assays known in the art. For example, typical symptoms of a MEK inhibitor-associated cutaneous condition such as acneiform rash (papulopustular rash), paronychia with or without pyogenic granulomas, and/or telangiectasia include, but are not limited to, abnormal scalp hair growth, abnormal facial hair growth, abnormal hair growth, abnormal eyelash growth, flesh-colored papules, dilated follicular or eccrine orifices, pruritis, erythema, pustules, papules, erythematous, pus collection, swollen, thickened nail plates, itching, threadlike red marks on skin, pain, nosebleeds, blood in stool, shortness of breath, seizures, small strokes, port-wine stain birthmarks, and anemia.

In some embodiments, subjects with a disease or condition characterized by elevated expression levels and/or increased activity of BRAF, and/or subjects suffering from a MEK inhibitor-associated cutaneous condition such as acneiform rash (papulopustular rash), paronychia with or without pyogenic granulomas, and/or telangiectasia that are treated with at least one BRAF inhibitor will show amelioration or elimination of one or more of the following symptoms: abnormal scalp hair growth, abnormal facial hair growth, abnormal hair growth, abnormal eyelash growth, flesh-colored papules, dilated follicular or eccrine orifices, pruritis, erythema, pustules, papules, erythematous, pus collection, swollen, thickened nail plates, itching, threadlike red marks on skin, pain, nosebleeds, blood in stool, shortness of breath, seizures, small strokes, port-wine stain birthmarks, and anemia.

In certain embodiments, subjects with a disease or condition characterized by elevated expression levels and/or increased activity of BRAF, and/or subjects suffering from a MEK inhibitor-associated cutaneous condition such as acneiform rash (papulopustular rash), paronychia with or without pyogenic granulomas, and/or telangiectasia that are treated with at least one BRAF inhibitor will show increased MAPK activation compared to untreated subjects suffering from a MEK inhibitor-associated cutaneous condition such as acneiform rash (papulopustular rash), paronychia with or without pyogenic granulomas, and/or telangiectasia.

Prophylactic Methods

In one aspect, the present technology provides a method for preventing or delaying the onset of a disease or condition characterized by elevated expression levels and/or increased activity of BRAF. Additionally or alternatively, in some embodiments, the present technology includes methods for preventing or delaying the onset of a MEK inhibitor-associated cutaneous condition such as acneiform rash (papulopustular rash), paronychia with or without pyogenic granulomas, and/or telangiectasia.

Subjects at risk or susceptible to a disease or condition characterized by elevated expression levels and/or increased activity of BRAF, and/or subjects at risk or susceptible to a MEK inhibitor-associated cutaneous condition include cancer patients that receive MEK inhibitor therapy. Such subjects can be identified by, e.g., any or a combination of diagnostic or prognostic assays known in the art.

In prophylactic applications, pharmaceutical compositions or medicaments comprising at least one BRAF inhibitor disclosed herein are administered to a subject susceptible to, or otherwise at risk of a disease or condition characterized by elevated expression levels and/or increased activity of BRAF, and/or a subject susceptible to, or otherwise at risk of a MEK inhibitor-associated cutaneous condition such as acneiform rash (papulopustular rash), paronychia with or without pyogenic granulomas, and/or telangiectasia, in an amount sufficient to eliminate or reduce the risk, or delay the onset of the disease, including biochemical, histologic and/or behavioral symptoms of the disease, its complications and intermediate pathological phenotypes presenting during development of the disease. Administration of a prophylactic BRAF inhibitor can occur prior to the manifestation of symptoms characteristic of the disease or disorder, such that the disease or disorder is prevented or, alternatively, delayed in its progression.

In some embodiments, treatment with the at least one BRAF inhibitor will prevent or delay the onset of one or more of the following symptoms: abnormal scalp hair growth, abnormal facial hair growth, abnormal hair growth, abnormal eyelash growth, flesh-colored papules, dilated follicular or eccrine orifices, pruritis, erythema, pustules, papules, erythematous, pus collection, swollen, thickened nail plates, itching, threadlike red marks on skin, pain, nosebleeds, blood in stool, shortness of breath, seizures, small strokes, port-wine stain birthmarks, and anemia. In certain embodiments, (a) subjects with a disease or condition characterized by elevated expression levels and/or increased activity of BRAF, and/or (b) subjects with a MEK inhibitor-associated cutaneous condition such as acneiform rash (papulopustular rash), paronychia with or without pyogenic granulomas, and/or telangiectasia that are treated with the at least one BRAF inhibitor will show BRAF expression levels that resemble those observed in healthy control subjects.

For therapeutic and/or prophylactic applications, a composition comprising at least one BRAF inhibitor disclosed herein, is administered to the subject. In some embodiments, the at least one BRAF inhibitor is administered one, two, three, four, or five times per day. In some embodiments, the at least one BRAF inhibitor is administered more than five times per day. Additionally or alternatively, in some embodiments, the at least one BRAF inhibitor is administered every day, every other day, every third day, every fourth day, every fifth day, or every sixth day. In some embodiments, the at least one BRAF inhibitor is administered weekly, bi-weekly, tri-weekly, or monthly. In some embodiments, the at least one BRAF inhibitor is administered for a period of one, two, three, four, or five weeks. In some embodiments, the at least one BRAF inhibitor is administered for six weeks or more. In some embodiments, the at least one BRAF inhibitor is administered for twelve weeks or more. In some embodiments, the at least one BRAF inhibitor is administered for a period of less than one year. In some embodiments, the at least one BRAF inhibitor is administered for a period of more than one year. In some embodiments, the at least one BRAF inhibitor is administered throughout the subject's life.

In some embodiments of the methods of the present technology, the at least one BRAF inhibitor is administered daily for 1 week or more. In some embodiments of the methods of the present technology, the at least one BRAF inhibitor is administered daily for 2 weeks or more. In some embodiments of the methods of the present technology, the at least one BRAF inhibitor is administered daily for 3 weeks or more. In some embodiments of the methods of the present technology, the at least one BRAF inhibitor is administered daily for 4 weeks or more. In some embodiments of the methods of the present technology, the at least one BRAF inhibitor is administered daily for 6 weeks or more. In some embodiments of the methods of the present technology, the at least one BRAF inhibitor is administered daily for 12 weeks or more. In some embodiments, the at least one BRAF inhibitor is administered daily throughout the subject's life.

Determination of the Biological Effect of the BRAF Inhibitors of the Present Technology In various embodiments, suitable in vitro or in vivo assays are performed to determine the effect of a specific BRAF inhibitor and whether its administration is indicated for treatment. In various embodiments, in vitro assays can be performed with representative animal models, to determine if a given BRAF inhibitor exerts the desired effect on reducing or eliminating signs and/or symptoms of MEK inhibitor-associated cutaneous conditions. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects. In some embodiments, in vitro or in vivo testing is directed to the biological function of one or more BRAF inhibitors.

Animal models of MEK inhibitor-associated cutaneous conditions may be generated using techniques known in the art. Such models may be used to demonstrate the biological effect of BRAF inhibitors in the prevention and treatment of conditions arising from disruption of a particular gene, and for determining what comprises a therapeutically effective amount of the one or more BRAF inhibitors disclosed herein in a given context.

Modes of Administration and Effective Dosages

Any method known to those in the art for contacting a cell, organ or tissue with at least one or more BRAF inhibitors disclosed herein may be employed. Suitable methods include in vitro, ex vivo, or in vivo methods. In vivo methods typically include the administration of at least one or more BRAF inhibitors to a mammal, suitably a human. When used in vivo for therapy, the at least one or more BRAF inhibitors described herein are administered to the subject in effective amounts (i.e., amounts that have desired therapeutic effect). The dose and dosage regimen will depend upon the degree of the disease state of the subject, the characteristics of the particular BRAF inhibitor used, e.g., its therapeutic index, and the subject's history.

The effective amount may be determined during pre-clinical trials and clinical trials by methods familiar to physicians and clinicians. An effective amount of one or more BRAF inhibitors useful in the methods may be administered to a mammal in need thereof by any of a number of well-known methods for administering pharmaceutical compounds. The BRAF inhibitors may be administered systemically or locally.

The one or more BRAF inhibitors described herein can be incorporated into pharmaceutical compositions for administration, singly or in combination, to a subject for the treatment or prevention of a MEK inhibitor-associated cutaneous condition. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The pharmaceutical compositions having one or more BRAF inhibitors disclosed herein can include a carrier, which can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

A therapeutic agent can be formulated in a carrier system. The carrier can be a colloidal system. The colloidal system can be a liposome, a phospholipid bilayer vehicle. In one embodiment, the therapeutic agent is encapsulated in a liposome while maintaining the agent's structural integrity. One skilled in the art would appreciate that there are a variety of methods to prepare liposomes. (See Lichtenberg, et al., *Methods Biochem. Anal.*, 33:337-462 (1988); Anselem, et al., *Liposome Technology*, CRC Press (1993)). Liposomal formulations can delay clearance and increase cellular uptake (See Reddy, *Ann. Pharmacother.*, 34(7-8): 915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic agent can be embedded in the polymer matrix, while maintaining the agent's structural integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother* 34(7-8):915-923 (2000)). A polymer formulation for human growth hormone (hGH) has been used in clinical trials. (See Kozarich and Rich, *Chemical Biology*, 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods,* 4(3): 201-9 (1994); and Gregoriadis, "Engineering Liposomes for Drug Delivery: Progress and Problems," *Trends Biotechnol.,* 13(12):527-37 (1995). Mizguchi, et al., *Cancer Lett.,* 100: 63-69 (1996), describes the use of fusogenic liposomes to deliver a protein to cells both in vivo and in vitro.

Dosage, toxicity and therapeutic efficacy of any therapeutic agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of the at least one or more BRAF inhibitors disclosed herein sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of the therapeutic compound ranges from 0.001-10,000 micrograms per kg body weight. In one embodiment, at least one or more BRAF inhibitor concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In some embodiments, a therapeutically effective amount of one or more BRAF inhibitors may be defined as a concentration of inhibitor at the target tissue of $10^{-32}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance with the present methods can be any mammal, including, for example, farm animals, such as sheep, pigs, cows, and horses; pet animals, such as dogs and cats; laboratory animals, such as rats, mice and rabbits. In some embodiments, the mammal is a human.

Kits

The present disclosure provides kits for use in treating or preventing a cutaneous condition that is induced by, caused by, or associated with treatment with MEK inhibitor, the kit including a composition comprising a therapeutically effective amount of at least one BRAF-inhibitor and instructions for use. In some embodiments, the composition is a pharmaceutical composition. Additionally or alternatively, in some embodiments, the pharmaceutical composition is provided in a suitable dosage form. Additionally or alternatively, in some embodiments, the dosage form is selected from systemic and topical. Additionally or alternatively, in some embodiments, the topical dosage form may be selected from, but not limited to: ointment, cream, gel, hydrogel, balm, spray, dermal patch, lotion, bandage, liquid, or any combinations thereof. Each possibility is a separate embodiment. Additionally or alternatively, in some embodiments, the systemic dosage form is oral form, selected from, but not limited to: tablet, capsule, liquid, suspension and powder, or any combination thereof. Each possibility is a separate embodiment. The above described components of the kits of the present technology may be packed in suitable containers and labeled for the treatment and/or prevention of MEK inhibitor-associated cutaneous conditions.

The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic products, that contain information about, for example, the indications, usage, dosage, manufacture, administration, contraindications and/or warnings concerning the use of such therapeutic or diagnostic products.

The kit can also comprise, e.g., a buffering agent, a preservative or a stabilizing agent. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit. In certain embodiments, the use of the reagents can be according to the methods of the present technology.

EXAMPLES

The present technology is further illustrated by the following Examples, which should not be construed as limiting in any way.

Example 1: Materials and Methods for Detecting ERK Phosphorylation in Primary Human Keratinocytes Normal human keratinocytes HEKa (purchased from Gibco Rhenium) were seeded in 10 cm dishes (300,000 cells/dish) and incubated overnight at 37° C., 5% $CO_2$. The medium was then replaced with a starvation medium for 2 hours and the cells were subsequently treated for 2 additional hours with the test compounds (i.e BRAF inhibitors). BRAF inhibitors used in the experiments included, LUT001, LUT156, LUT192, LUT195, LUT197 or vemurafenib as a control, at concentrations of 0.3 mM or 1 mM.

Post incubation, the cells were lysed with RIPA buffer and the protein extracts were analyzed by Western blot to detect Phospho-ERK and total ERK using suitable antibodies. Untreated cells and 0.1% DMSO treated cells were used as negative control and Human Keratinocyte Growth Supplement (HKGS) (Gibco) was used as a positive control.

Western Blot: 7.5 μg of total extract was loaded on 10% or 12% acrylamide gel. Following transfer, the membranes were blocked with TBST/5% skimmed milk and then incubated with Mouse anti Phospho-ERK (1:1000 in TBST 5% BSA, ON at 4° C.) and goat anti Mouse HRP (1:10,000 in TBST 5% BSA, 1-hour RT). The membranes were exposed using SuperSignal West Pico Chemiluminescent Substrate.

HRP was subsequently inactivated by incubating the membranes for 1 hour with 0.5% sodium azide. Following washes and ECL exposure in order to ensure absence of signal, the membranes were re-blocked for 15 min with TBST/5% skimmed milk and then incubated with Rabbit anti total ERK2 (1:500 in TBST 5% BSA, ON at 4° C.), goat anti Rabbit HRP (1:5,000 in TBST 5% BSA, 1-hour RT) and finally exposed using the SuperSignal West Pico Chemiluminescent Substrate. The films were scanned and the signal was quantified using ImageJ software. The results were calculated as Phospho-ERK/total ERK.

Example 2: Activation of MAPK (ERK) by Various BRAF Inhibitors in Normal Human Keratinocytes (HEKa)

In this experiment, the effect of the BRAF inhibitor compounds disclosed herein on MAPK (ERK) phosphorylation in human keratinocytes (HEKa) was investigated. Phosphorylation of ERK served as an indicator for ERK activation.

In order to determine the effect of various BRAF inhibitors on ERK activation in relevant keratinocytes cells, the level of ERK phosphorylation was measured in normal human keratinocytes in response to treatment with the BRAF inhibitors.

As shown in FIGS. 1A-D, significant ERK activation (as determined by an increase in the relative amount of Phosphorylated ERK) was observed in human primary keratinocytes (HEKa) following treatment with LUT156, LUT197 (FIGS. 1A and 1C) or vemurafenib (FIGS. 1B and 1D) BRAF inhibitors. Treatment with LUT001, LUT192, and LUT195 resulted in a moderate effect on ERK activation in HEKa.

These results demonstrate the unexpected paradoxical effect of various BRAF inhibitors with respect to activating downstream MAPK (ERK) in keratinocytes cells. Further, the results demonstrate the different efficacies of various BRAF inhibitors at varying dosages (concentration) with respect to activating ERK. Accordingly, the BRAF inhibitor compositions of the present technology are useful in methods for treating or preventing MEK inhibitor-associated cutaneous conditions in a subject.

Example 3: Effect of BRAF Inhibitors on the Proliferation of MIA PaCa2 KRAS Cells A proliferation assay will be conducted using MIA PaCa2 cell lines harboring a KRAS mutation to determine whether BRAF inhibitors will have a durable effect.

Materials. MIA PaCa2 KRAS cells (ATCC, CRM-CRL1420); DMEM (ATCC 30-2002); FBS (Biol. Industries, Cat. 04-007-1A); Horse serum (Biol. Industries, Cat. 04-004-1B), Antibiotics (P/S, Biol. Industries, Cat. 03-031-2B), Trypsin (Biol. Industries, Cat. 03-050-1A), Trypan Blue (Sigma T8154); DMSO (Sigma D2650), BRAF inhibitors (C-1 MedChem Express (HY-14177); C-15; C-19; Vemurafenib (Royal Pharma)), ATPlite (Perkin Elmer, Cat. 6016941).

Cell Growth: On day 1, the cells will be placed in culture media (DMED/FBS/Horse serum and antibiotics). Subsequently, the cells will be sub-cultured and incubated for 24 hours in a starvation medium (i.e., serum depleted medium). The test compounds (BRAF inhibitors) will be added to the cells at various concentrations and the cells will be incubated (at 37° C., 5% $CO_2$) for an additional 72 hours. A proliferation assay will be performed using the ATPlite reagent, according to manufacturer protocol. The results will be read using CLARIOstar (BMG) reader (Mode: Luminescence, program: ATPlite TOP, Measurement interval time [s]: 0.25-1).

It is anticipated that treatment with BRAF inhibitors will increase proliferation in MIA PaCa2 KRAS cells compared to that observed in untreated MIA PaCa2 KRAS control cells.

Example 4: Use of BRAF Inhibitors to Treat a MEK Inhibitor-Associated Cutaneous Condition in a Subject Subjects that have been diagnosed with MEK inhibitor-associated cutaneous conditions (i.e., subjects that have been or are being treated with MEK inhibitors) will be treated with BRAF inhibitors to determine in vivo efficacy. A placebo treated group (vehicle) will be included as a negative control.

Briefly, the treatment protocol includes the following steps:

Subjects are patients that have been treated with a MEK inhibitor and have been diagnosed with cutaneous conditions, (including acneiform rash). The subjects are treated for 6-20 weeks with a BRAF inhibitor in a suitable dosage form, on one body side, face, neck and chest. The dosage form may include a topical dosage form. Different concentrations of the BRAF inhibitor will be tested. Control subjects are treated with a suitable placebo composition, which does not include a BRAF inhibitor as an active substance. When applied topically, the placebo treatment is performed on the other body side which is not being treated. During the treatment period, various parameters are tested, including, the rate of the cutaneous condition eruptions, the severity of the eruptions, the body location of the eruptions and other related cutaneous events. The body locations tested will include the face, neck and chest.

At the end of the trial treatment period, the tested parameters are determined by comparing the treated body regions with the placebo-treated regions (for topical administration), or between treated and placebo treated (for systemic administration) to determine treatment efficacy.

It is anticipated that the body regions treated with the BRAF inhibitor will show amelioration in the rate and/or severity of eruptions and/or other cutaneous events compared to that observed with the placebo-treated regions. Accordingly, the BRAF inhibitor compositions of the present technology are useful in methods for treating or preventing MEK inhibitor-associated cutaneous conditions in a subject.

Example 5: In Vitro Effect of a BRAF Inhibitor on Phospho-ERK Following Administration of MEK Inhibitors HEKa cells will be treated with a BRAF inhibitor and a MEK inhibitor (e.g., Trametinib and Cobimetinib), using the methods described in Example 1. HKGS treated HEKa cells serve as a positive control and DMSO treated HEKa cells serve as an untreated control. The effect of BRAF inhibitor and MEK inhibitors on Phospho-ERK will be measured by Western blot as described in Example 1. Controls for comparing the effect of BRAF inhibitors following administration of MEK inhibitors on Phospho-ERK are shown below.

|  | Phospho-ERK | Total ERK | Phospho/Total Ratio | % of Control |
|---|---|---|---|---|
| DMSO (3.75 µl) | 539.971 | 7316.397 | 0.07 | 100 |
| HKGS | 9391.983 | 7094.569 | 1.32 | 1793.7 |

The addition of Trametinib (MEK inhibitor) to HKGS treated cells is expected to decrease the levels of Phospho-ERK compared to HKGS alone. BRAF inhibitors are expected to increase the Phospho-ERK by about 100% to about 800% as compared to the DMSO treated cells. The BRAF inhibitor is expected to increase Phospho-ERK levels when added to cells treated with HKGS and Trametinib. The BRAF inhibitor is expected to increase Phospho-ERK levels when added to cells treated with HKGS and Cobimetinib. The observed increase in ERK activation will correlate with the therapeutic efficacy of a BRAF inhibitor in treating or ameliorating a MEK inhibitor-associated cutaneous condition. Accordingly, the BRAF inhibitor compositions of the present technology are useful in methods for treating or preventing MEK inhibitor-associated cutaneous conditions in a subject.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A method of treating or preventing a MEK inhibitor-associated cutaneous condition in a subject in need thereof comprising administering to the subject an effective amount of LUT197 or LUT156, thereby treating the MEK inhibitor-associated cutaneous condition, wherein the MEK inhibitor is selected from the group consisting of Trametinib (GSK1120212), Cobimetinib (XL518), Binimetinib (MEK162), Selumetinib, PD-325901, CI-1040, PD035901, UO126, TAK-733, and any combination thereof.

2. The method of claim 1, wherein administration of LUT197 or LUT156 results in an increase in MAPK activation in the subject compared to that observed in the subject prior to administration.

3. The method of claim 1, wherein the MEK inhibitor-associated cutaneous condition is selected from the group consisting of abnormal scalp hair growth, abnormal facial hair growth, abnormal hair growth, abnormal eyelash growth, acneiform rash (papulopustular rash), paronychia with or without pyogenic granulomas, and telangiectasia.

4. The method of claim 3, wherein the signs or symptoms of acneiform rash (papulopustular rash) comprise one or more of flesh-colored papules, dilated follicular, eccrine orifices, pruritis, erythema, pustules, or papules.

5. The method of claim 3, wherein the signs or symptoms of paronychia with or without pyogenic granulomas comprise one or more of erythematous, pus collection, swollen, or thickened nail plates.

6. The method of claim 3, wherein the signs or symptoms of telangiectasia comprise one or more of itching, threadlike red marks on skin, pain, nosebleeds, blood in stool, shortness of breath, seizures, small strokes, port-wine stain birthmarks, or anemia.

7. The method of claim 1, wherein the MEK inhibitor-associated cutaneous condition is acneiform rash.

8. The method of claim 1, wherein the subject is treated with a MEK inhibitor prior to administration of LUT197 or LUT156.

9. The method of claim 1, wherein LUT197 or LUT156 is administered orally, topically, intranasally, systemically, intravenously, subcutaneously, intraperitoneally, intradermally, intraocularly, iontophoretically, transmucosally, or intramuscularly, or wherein LUT197 or LUT156 is locally administered to the skin of the subject.

10. A method of treating or preventing acneiform rash in a subject in need thereof, comprising administering to the subject an effective amount of LUT197 or LUT156, wherein the acneiform rash is a side effect caused by treating the subject with a MEK inhibitor and wherein the MEK inhibitor is selected from the group consisting of Trametinib (GSK1120212), Cobimetinib (XL518), Binimetinib (MEK162), Selumetinib, PD-325901, CI-1040, PD035901, UO126, TAK-733, and any combination thereof.

11. The method of claim 10, wherein the LUT197 or LUT156 is administered orally, topically, intranasally, systemically, intravenously, subcutaneously, intraperitoneally, intradermally, intraocularly, iontophoretically, transmucosally, or intramuscularly.

* * * * *